(12) United States Patent
Kim et al.

(10) Patent No.: US 8,986,675 B2
(45) Date of Patent: Mar. 24, 2015

(54) COMPOSITIONS AND METHODS FOR PREVENTION AND TREATMENT OF OBESITY AND OBESITY RELATED METABOLIC SYNDROME

(75) Inventors: Hyeon Jin Kim, Jeollabuk-do (KR); Seong Tshool Hong, Jeollabuk-do (KR)

(73) Assignee: Jinis Biopharmaceuticals Co., Jeollabuk-Do (KR)

( * ) Notice: Subject to any disclaimer, the term of this patent is extended or adjusted under 35 U.S.C. 154(b) by 259 days.

(21) Appl. No.: 13/255,838

(22) PCT Filed: Jun. 5, 2009

(86) PCT No.: PCT/KR2009/003036
§ 371 (c)(1),
(2), (4) Date: Oct. 17, 2011

(87) PCT Pub. No.: WO2010/104242
PCT Pub. Date: Sep. 16, 2010

(65) Prior Publication Data
US 2012/0121753 A1    May 17, 2012

(30) Foreign Application Priority Data
Mar. 10, 2009  (KR) .......... 10-2009-0020474

(51) Int. Cl.
*C12N 1/20* (2006.01)
*C12N 1/00* (2006.01)
*A01N 63/00* (2006.01)
*A61K 35/74* (2006.01)

(52) U.S. Cl.
CPC ............... *A61K 35/74* (2013.01); *A61K 35/747* (2013.01); *Y10S 435/854* (2013.01)
USPC ..... 424/93.45; 424/93.1; 435/243; 435/252.9; 435/854

(58) Field of Classification Search
USPC .................................. 424/93.45; 435/252.9
See application file for complete search history.

(56) References Cited

U.S. PATENT DOCUMENTS 6,080,401 A * 6/2000 Reddy et al. .................. 424/93.3
6,808,703 B2 * 10/2004 Park et al. .................... 424/93.4

FOREIGN PATENT DOCUMENTS

| KR | 10-2004-0027180 A | 4/2004 |
| KR | 10-2005-0059860 A | 6/2005 |
| KR | 10-0543114 B1 | 1/2006 |
| KR | 10-0851586 B1 | 8/2008 |

OTHER PUBLICATIONS

Drew et al., "Obesity management: Update on orlistat", Vasc. Health Risk Manag. 3, pp. 817-821 (2007).
Kopelman et al., "Obesity as a medical problem", Nature 404, pp. 635-643 (2000).
Must et al., "The Disease Burden Associated With Overweight and Obesity", J. Am. Med. Assoc. 282, pp. 1523-1529 (1999).
Rucker et al., "Long term pharmacotherapy for obesity and overweight: updated meta-analysis", Cochrane Database Syst. Rev. 3, BMJ ONLINE FIRST bmj.com (2003). (10 pages).
Padwal et al., "Drug treatments for obesity: orlistat, sibutramine, and rimonabant" Lancet 369, pp. 71-77 (2007).
Rolls et al., "Sibutramine Reduces Food Intake in Non-Dieting Women with Obesity", Obes. Res. 6, pp. 1-11 (1998).
Bray et al., "Sibutramine Produces Dose-Related Weight Loss", Obes. Res. 7, pp. 189-198 (1999).
Guercolini "Mode of Action of Orlistat", Int. J. Obes. Relat. Metab. Disord. 21, pp. S12-S23 (1997).
Hauptman et al., "Initial studies in humans with the novel gastrointestinal lipase inhibitor Ro 18-0647 (tetrahydrolipstatin)1'2" Am. J. Clin. Nutr. 55, pp. 309S-313S (1992).
Hill et al., "Orlistat, a lipase inhibitor, for weight maintenance after conventional dieting: a 1-y study1-3", Am.J.Clin. Nutr. 69, pp. 1108-1116 (1999).
Ley et al., "Human gut microbes associated with obesity" Nature 444, pp. 1022-1023 (2006).
Turnbaugh et al., "An obesity-associated gut microbiome with increased capacity for energy harvest" Nature 444, pp. 1027-1031 (2006).
Turnbaugh et al., "Diet-Induced Obesity Is Linked to Marked but Reversible Alterations in the Mouse Distal Gut Microbiome", Cell Host Microbe 3, pp. 213-223 (2008).
Lin et al., "Viable counts, characteristic evaluation for commercial lactic acid bacteria products", Food Microb. 23, pp. 74-81 (2006).
Johannson et al., "Administration of Different *Lactobacillus* Strains in Fermented Oatmeal Soup: In Vivo Colonization of Human Intestinal Mucosa and Effect on the Indigenous Flora", Appl. Environ. Microbiol. 59, pp. 15-20 (1993).
Leenan et al., "Visceral fat accumulation in obese subjects: relation to energy expenditure and response to weight loss", R.Am.J.Physiol. 263, pp. E913-E919 (1992).
Keno et al., "High Sucrose Diet Increases Visceral Fat Accumulation in VMH-Lesioned Obese Rats", Int. J. Obes. 15, pp. 205-211 (1991).
Molavi et al., "The prevention and treatment of metabolic syndrome and high-risk obesity", Curr. Opin. Cardiol. 21, pp. 479-485 (2006).

(Continued)

*Primary Examiner* — Vera Afremova
(74) *Attorney, Agent, or Firm* — Susan Paik (57) ABSTRACT

The present invention relates to the prevention and treatment of obesity and obesity related metabolic syndrome, particularly to the prevention and treatment of obesity by changing intestinal flora. The characteristics of intestinal bacteria are transformed by administration of a microorganism preparation which improves free fatty acid absorption by the bacteria, and free fatty acid absorption in the gastrointestinal tract is thereby decreased by introduction thereof. The present invention provides a method for preventing and treating obesity and obesity related metabolic syndrome, a pharmaceutical composition and diet supplement for prevention and treatment thereof, and modified probiotic strains usable for such purposes. The present invention provides a weight loss effect and shows that the absorption of fatty acids in the gastrointestinal tract is blocked by improving the characteristics of intestinal bacteria and transplanting them, thereby enabling the treatment of obesity.

2 Claims, 6 Drawing Sheets

(56) References Cited

OTHER PUBLICATIONS

Spiotta et al., "Evaluating Obesity and Cardiovascular Risk Factors in Children and Adolescents", Am. Fam. Physician 78, pp. 1052-1058 (2008).

Rand "Obesity and Caloric Intake", J. Chronic Dis. 40, p. 911 (1987).

National Heart Lung and Blood Institute, "Clinical Guidelines on the Identification, Evaluation, and Treatment of Overweight and Obesity in Adults" Obes. Res. 6, (1998) NIH Publication No. 98-4083 Sep. 1998. (262 pages).

Hill "Understanding and Addressing the Epidemic of Obesity: An Energy Balance Perspective" Endocr. Rev. 27, pp. 750-761 (2006).

Thompson-Chagoyon et al., "Colonization and Impact of Disease and Other Factors on Intestinal Microbiota", Dig. Dis. Sci. 52, pp. 2069-2077 (2007).

Stecher "The role of microbiota in infectious disease", Trends. Microbiol. 16, pp. 107-114 (2008).

Isolauri et al., "Modulation of the Maturing Gut Barrier and Microbiota: A Novel Target in Allergic Disease" Curr. Pharm. Des. 14, pp. 1368-1375 (2008).

Jia "Gut microbiota: a potential new territory for drug targeting" Nature Rev. Drug Disc. 7, pp. 123-131 (2008).

\* cited by examiner

COMPOSITIONS AND METHODS FOR PREVENTION AND TREATMENT OF OBESITY AND OBESITY RELATED METABOLIC SYNDROME

BACKGROUND

1. Technical Field

This invention relates to compositions and methods for prevention and treatment of obesity and obesity related metabolic syndrome using microorganisms.

2. Description of Related Art

Obesity is an epidemic, stigmatized, and costly disease that is rarely curable and is increasing in prevalence in most of the world. It poses a major risk for various serious chronic diseases. Excess weight poses major risks for a number of serious metabolic diseases, such as hypertension, type II diabetes, dyslipidemia, arteriosclerosis, ischemic heart disease, fatty liver disease, gallstones, osteoarthritis, reproductive and gastrointestinal cancers, and sleep apnea. The main prescription products currently approved for obesity are sibutramine (Abbott's Meridia®) and Orlistat™ (Roche's Xenical™). Sibutramine inhibits the re-uptake of noradrenaline and serotonin, controlling appetite and therefore decreasing food intake. Sibutramine, however, has well known side effects associated with sympathomimetic properties, affecting heart rate and blood pressure. In contrast to sibutramine, Orlistat™ acts locally. Orlistat™ is a gastric and pancreatic lipase inhibitor that prevents fat hydrolysis, thus reduces dietary fat absorption by approximately 30%. However, undigested fat along the gastrointestinal tract causes side effects, which is not only uncomfortable but also socially unacceptable. Therefore, a new type of anti-obesity treatment needs to be actively sought because the current pharmaceutical drugs are not ideal for the treatment of obesity.

REFERENCES CITED

1. B. S. Drew, A. F. Dixon, J. B. Dixon, *Vasc. Health Risk Manag.* 3, 817 (2007)
2. P. G. Kopelman, *Nature* 404, 635 (2000)
3. Must et al., *J. Am. Med. Assoc.* 282, 1523 (1999)
4. R. Padwal, S K Li, D C Lau, Cochrane *DatabaseSyst. Rev.* 3, CD004094 (2003)
5. R. S. Padwal, S. R. Majumdar, *Lancet* 369, 71 (2007)
6. J. Rolls, D. J. Shide, M. L. Thorwart, J. S. Ulbrecht, *Obes. Res.* 6, 1 (1998)
7. G. A. Bray et al., *Obes. Res.* 7, 189 (1999)
8. R. Guercolini, Int. J. Obes. Relat. Metab. Disord. 21, S12 (1997)
9. J. B. Hauptman, F. S. Jeunet, D. Hartmann, *Am. J. Clin. Nutr.* 55, 309S(1992)
10. J. O. Hill, et al., *Am. J. Clin. Nutr.* 69, 1108 (1999)
11. R. E. Ley, P. J. Turnbaugh, S. Klein, J. I. Gordon, *Nature* 444, 1022 (2006)
12. P. J. Turnbaugh, R. E. Ley, M. A. Mahowald, V. Magrini, E. R. Mardis, J. I. Gordon, Nature 444, 1027 (2006)
13. P. J. Turnbaugh, F. Backhed, L. Fulton, J. I. Gordon, *Cell Host Microbe* 3, 213 (2008)
14. W. H. Lin, C. F. Hwang, et al., *Food Microb.* 23, 74 (2006)
15. *Appl Environ Microbiol.* 59, 15 (1993)
16. R. Leenen et al., *Am. J. Physiol.* 263, E913 (1992)
17. Y. Keno et al., *Int. J. Obes.* 15, 205 (1991)
18. Molavi, N. Rasouli, P. A. Kern, *Curr. Opin. Cardiol.* 21, 479 (2006).
19. R. T. Spiotta, G. B. Luma, *Am. Fam. Physician* 78, 1052 (2008)
20. S. Rand, *J. ChronicDis.* 40, 911 (1987)
21. National Heart Lung and Blood Institute, *Obes. Res.* 6; 51S(1998)
22. J. O. Hill, *Endocr. Rev.* 27, 750 (2006)23. C. Thompson-Chagoyon, J. Maldonado, A. Gil, *Dig. Dis. Sci.* 52, 2069 (2007)
23. C. Thompson-Chagoyon, J. Maldonado, A. Gil, *Dig. Dis. Sci.* 52, 2069 (2007)
24. B. Stecher, W. D. Hardt, *Trends. Microbiol.* 16, 107 (2008)
25. Isolauri, M. Kalliomaki, K. Laitinen, S. Salminen, *Curr Pharm Des.* 14, 1368 (2008)
26. W. Jia, H. Li, L. Zao, J. K. Nicholson, *Nature Rev. Drug Disc.* 7, 123 (2008)

SUMMARY OF THE INVENTION

Technical Problem

Recent evidence showed that gut microbiota plays an intricate role in the regulation of body weight (11-13). The transplantation experiments of the microbiota from obese and lean mice into microbe-free mice also proved that the compositional change of microbiota in the gastrointestinal (GI) tract resulted in differences in the efficiency of caloric extraction from food, eventually contributing to differential body weights (12, 13). These results suggest that small changes in caloric extraction in the GI tract by xenobiotically manipulated intestinal bacteria can lead to a meaningful reduction in body weight. Given that fat is degraded as fatty acid (FA) before absorption into body, removal of FA in the GI tract by the transplantation of a FA-extracting bacterium might be an idea for decreasing fat uptake by host body to treat obesity. In fact, reduction of dietary fat uptake in body by removing available FA is a better choice than by inhibiting fat hydrolysis that result in unavoidable undigested fat problem.

It's an object of the present invention to provide prevention or treatment of obesity and obesity related metabolic syndrome using microorganisms. Particularly, this invention provides a method and pharmaceutical compositions for reducing the dietary intake of fat by removing fatty acids for absorption. It is another object of the present invention to provide pharmaceutical compositions for obesity without side effects, unlike current pharmaceutical drugs, sibutramine and Orlistat™.

Technical Solution

In this invention, a probiotic strain, *Lactobacillus acidophilus*, was mutagenized to isolate a mutant that has enhanced capacity for FA removal. Administration of this fatty acid robbing microbe, FARM, to rats resulted in weight loss that was equal to that caused by the most popular anti-obesity pharmaceutical, Orlistat™. Therefore, this invention provides a method to reduce FA absorption in the GI tract by administration of probiotic strain with enhanced capacity for FA absorption and thus its removal from the GI tract of the host. This invention provides a microbial drug for obesity.

Based on experimental data, this invention provides a pharmaceutical composition for prevention or treatment of obesity and obesity related metabolic syndrome, comprising microorganisms which can colonize and extract free fatty acids in the gastrointestinal tract of mammals. Preferably, the microorganisms are from gut microbiota or derived from gut microbiota. More preferably, the micoorganisms are probiotic strains.

In the examples of this invention, *Lactobacillus acidophilus* FARM 1 KCTC 11513BP, *Lactobacillus acidophilus*

FARM2 KCTC 11514BP, *Lactobacillus acidophilus* FARM3 KCTC 11515BP are obtained from a commercial probiotic strain, *Lactobacillus acidophilus*, by improving its capability of FA absorption.

This invention provides FARM which can colonize in the GI tract and has enhanced FA absorption capacity as active ingredient of dietary supplement for prevention or treatment of obesity and obesity related metabolic syndrome.

In this invention, the term "dietary supplement" is intended to mean any food with specific health function in addition to its nutrient function, including nutraceuticals, functional food, designer food, health food. The purpose of a dietary supplement according to an aspect of the present invention is in preventing or treating obesity and obesity related metabolic syndrome.

This invention also provides FARM which can colonize in the GI tract and has enhanced FA absorption capacity, *Lactobacillus acidophilus* FARM 1 KCTC 11513BP, *Lactobacillus acidophilus* FARM2 KCTC 11514BP, *Lactobacillus acidophilus* FARM3 KCTC 11515BP.

This invention also provides a method for treating obesity and obesity related metabolic syndrome by administration of FARM which can colonize in the GI tract and has enhanced FA absorption capacity. This invention provides an effective method for obesity and obesity related metabolic syndrome by reducing dietary energy intake after administration of FARM.

Advantageous Effects

Extra caloric intake from dietary fat is the most important determinant of obesity as it can be observed from rapid increases in underdeveloped countries. For the vast majority of humans, even caloric intake exceeding 1% more than caloric expenditure results in the accumulation of body fat, thereby leads to obesity.

This invention demonstrated that transplantation of xenobiotically manipulated *Lactobacillus*, FARM, actively extract FA in the GI tract to limit caloric intake by host, which showed anti-obesity effect as much as the most popular anti-obesity pharmaceutical drug, Orlistat™. Moreover, FARM as an anti-obesity drug has obvious advantages over the current pharmaceuticals for obesity. First, it does not act on the brain, but acts peripherally and, therefore, has a superior risk-benefit profile to centrally acting drugs, such as sibutramine. Second, FARM does not act on lipid hydrolysis that causes the unavoidable side effect of the GI tract such as anal leakage and oily spotting. Third, FARM is a *Lactobacillus* strain which is a beneficial probiotic and conveys considerable safety as a drug candidate.

Since gut microbiota is associated with various complex diseases such as infectious disease, obesity, cancer, allergic diseases etc., the transplantation of living intestinal bacteria xenobiotically modified into a host has strong potential to treat the various microbiota-related diseases. The present invention also proved the hypothesis that the transplantation of specifically manipulated intestinal bacteria can successfully change microbial flora in the GI tract to treat the diseases of a host.

DETAILED DESCRIPTION OF PREFERRED EMBODIMENTS

Best Mode

FARM Strain with Enhanced FA Absorption Capacity

A commercial probiotic strain, *Lactobacillus acidophilus* KCTC 3179 was mutagenized by N-methyl-N-nitro-N-nitrosoguanidine (NTG) to isolate mutants that has the increased capability of FA absorption. We initially isolated a mutant absorbing/robbing free fatty acid 2.1 times more from its surrounding environment than the wild type strain. The identified mutant, fatty acid robbing microbe 1 (FARM1) was deposited at Korean Collection for Type Cultures, Korea Research Institute of Bioscience and Biotechnology (KRIBB), 111 Gwahangno, Yuseong-gu, Daejeon 305-806, Republic of Korea, on May 19, 2009 under accession number KCTC 11513BP. FARM1 was again mutagenized by 4-nitroquinoline 1-oxide (4NQO) to isolate a mutant, FARM2, with more improved extraction of free FA. FARM2 was deposited at Korean Collection for Type Cultures, Korea Research Institute of Bioscience and Biotechnology (KRIBB), 111 Gwahangno, Yuseong-gu, Daejeon 305-806, Republic of Korea, on May 19, 2009 under accession number KCTC 11514BP. The mutagenesis yield the FARM2 mutant that absorbed $^{14}$C labeled palmitic acid up to 3.1 times more than the wild type strain. With the identified FARM strains, the abilities of acidification during its growth and colonization in host gastrointestinal tract after consumption were examined since these are the most important characteristics of edible *Lactobacillus*. Both mutants, FARM1 and FARM2, maintained normal growth and acidification activity during yogurt fermentation. The mutant strains also colonized successfully the GI tract of rats after administration of the mutants as a yogurt form. These results indicate that both FARM1 and FARM2 functions as a normal *Lactobacillus* except their capability of enhanced FA extraction.

Reduction of Caloric Intake by Host that was Colonized with FARMs which Extract Free FA in GI Tract Intestinal bacteria with an enhanced capacity for FA extraction could colonize the small intestine, where most FAs are absorbed into the body. The FARM could actively absorbs FAs in the small intestine and function as a bio-sequestrant, resulting in the removal of FAs that are available for absorption by the host's body. Subsequently, the FAs sequestered by the fast FA-extracting bacteria would be gradually transferred to the large intestine for fecal excretion, thereby reducing caloric extraction by the host.

To test whether FARMs actually extract fatty acid in the GI tract of a host to reduce caloric extraction by a host body, we fed the FARM-fermented yogurts into rats for 8 weeks to colonize the GI tract of the rats. After colonizing the GI tract of rats with FARMs and normal *Lactobacillus*, $^{14}C$ labeled triolein was orally administrated to rats to assess FA absorption in the rats by measuring radioactivity of FA, the digested product of $^{14}C$ labeled triolein, in their blood. The rats colonized with FARMs showed higher capability of FA extraction from its surrounding environment while it showed less FA uptake capability by their body in a dose dependant manner. The rats colonized with FARM1 and FARM2 reduced FA absorption up to 35% and 47%, respectively, compared to rats colonized with wild-type *Lactobacillus*. This result implies that both FARM1 and FARM2 successfully extracted absorbable FA in the GI tract of the rats, thereby reducing caloric extraction by host body.

The Effect of Caloric Extraction by FARMs in the GI Tract on Obesity

The effect of caloric extraction by FARMs in the GI tract on obesity was evaluated by feeding yogurt fermented with FARMs to male rats for 22 weeks while inducing obesity by diet. Daily administration of 3 ml of yogurt containing about $10^9$ CFU per ml of either wild-type *L. acidophilus* or FARMs, resulted in the successful colonization in the GI tract of the rats after 4 weeks. As expected, colonization of FARM1 and FARM2 in the rats reduced body weight gain up to 15% and 19%, each, compared to the rats colonized with 3179 strain.

Extra-caloric intake in mammals mainly accumulates as visceral fat so that the visceral fat is correlated with whole-body weight. In this work, we measured the visceral fat area using open-type 0.3 Tesla MRI at the end of feeding experiments. The visceral fat contents of the control rats without feeding any *Lactobacillus* and rats colonized with wild-type *L. acidophilus*, FARM1 or FARM2 were 27%, 24%, 14%, and 13%, respectively. These results clearly showed that colonization of the GI tract of rats with FARMs reduced both body weight gain and visceral fat accumulation, indicating that FARMs actually absorb FA in the GI tract of host. Consequently, it reduce FA intake by host, thereby reducing visceral fat accumulation and body weight gain.

Analysis of the Biochemical Parameters of Serum Relating to Metabolic Syndrome

Since obesity is associated with metabolic syndrome such as insulin resistance, glucose tolerance, dyslipidemia, coronary artery disease, etc., the biochemical parameters of serum relating to metabolic syndrome were analyzed at the end of feeding experiments. The levels of TG, TC and LDL-cholesterol in the control rats without feeding any *Lactobacillus* and rat colonized with wild-type *L. acidophilus* 3179, were higher than those in FARM1 and FARM2 groups while HDL-cholesterol levels were reversed, low in the control groups but high in the FARM groups. FARM strains also showed an anti-diabetic effect as expected from their anti-obesity effect.

Feeding FARM1 and FARM2 significantly reduced the serum insulin levels about 23% and 30%, respectively, compared to the untreated control. Also, FARM1 and FARM2 significantly reduced the average serum leptin levels to 20% and 45%, respectively, compared to the untreated control. The serum glucose levels were slightly lower in FARM1 and FARM2 group (107.6 mg/dl and 108.4 mg/dl), compared to untreated and 3179 control (122.1 mg/dl and 123.4 mg/dl). As a body gains weight, the body is known to become less sensitive to leptin and insulin as well as have a worsening plasma lipid profile, which leads to increased plasma concentrations of leptin, insulin, glucose, LDL cholesterol and total cholesterol. Our results showed that FARMs is effective in inhibiting insensitivity of insulin and leptin and improving the blood lipid profile by inhibiting the gain of body weight. The biochemical analyses on rat serums solidify the potential of FARM as an effective treatment for obesity.

The Possibility to Use FARM as a Living Anti-Obesity Drug

Because the mice colonized with FARMs showed reduction in FA absorption by a host to eventually inhibit body weight gain and visceral fat accumulation, we explored the possibility to use FARM as a living anti-obesity drug for diet-induced obesity after further improvement of free FA absorption capability of FARM. FARM2 went through $3^{rd}$ round mutagenesis with EMS to generate *Lactobacillus* with better fatty acid extraction capability. We were able to isolate a mutant, FARM3 that extracts free fatty acid 5 times faster than the wild type strain. FARM3 was deposited at Korean Collection for Type Cultures, Korea Research Institute of Bioscience and Biotechnology (KRIBB), 111 Gwahangno, Yuseong-gu, Daejeon 305-806, Republic of Korea, on May 19, 2009 under accession number KCTC 11515BP.

Daily administration of 3 ml of the yogurt fermented with FARM3 to male SD rats for 4 weeks resulted in reduction of body weight about 18%, compared to the wild-type *Lactobacillus* 3179 feeding group. The degree of body weight reduction by FARM3 were basically similar to those of the rat to which pharmaceutically effective dose of Orlistat™ was administered. Other than effective reduction of body weight, FARM3-feeding rats did not produce oily feces unlike Orlistat™ feeding group. These results implicate that FARM3 can be used as a living anti-obesity drug that is not only safe but also effective as much as pharmaceutical drugs.

The technological aspect of this invention is not limited to FARM or probiotics. It is clear to anybody with general knowledge that the technological aspect of this invention can be applied to any microbes which can colonize GI tract of mammals, especially human and contribute to the reduction in intake of dietary fat.

EXAMPLES

The present invention may be better understood with reference to the accompanying examples that are intended for purposes of illustration only and should not be construed to limit the scope of the invention, as defined by the claims appended hereto.

Reagents

Reagents were from Sigma™ except: [1-14C]-palmitic acid (PerkinElmer™ Life Sciences), liquid scintillation cocktail (LSC, PerkinElmer™ Life Sciences), [carboxyl-14C]-triolein (Research Products International™), Man-Rogosa-Sharpe (MRS, Difco), Orlistat™ (Xenical™, Roche). The sterilizable 384-well plate and 384-pin replicator were from Nunc™. Membrane semi-dry system was from Bio-Rad™. X-ray film was from Kodak™. Gel-Pro™ analyzer software was from Media Cybernetics™. *L. acidophilus* KCTC3179 is a human-derived *Lactobacillus* strain from the Korea Collection for Type Cultures (KCTC). Anaerobic culture was carried out in an anaerobic jar (BBL Gas-Pack anaerobic systems). Male Sprague-Dawley (SD) rats were obtained from Dae Han Biolink™ Co., Ltd. MRI images were obtained with a Bruker Biospec™ 47/40 4.7-Tesla instrument (Bruker) and analyzed with Image J (NIH). Serum was analyzed with a Rat/Mouse ELISA kit (LINCO™ research), a Leptin ELISA kit (R&D Systems™), a blood glucose meter (Accu-Chek™), and cholesterol ELISA kits (Asan™ Pharm. Co), respectively.

Obtaining FARM from Mutagenesis

*Lactobacillus* KCTC3179 cells were grown statically in MRS medium, pH 7.2, at 37° C. in a BBL Gas-Pack for anaerobic culture in this experiment, otherwise noted. Chemical mutagenesis of *Lactobacillus* KCTC3179 was performed as described below to obtain a FARM1 mutant. After 24 h culture of *Lactobacillus* KCTC317.9, the N-methyl-N-nitro-N-nitrosoguanidine (NTG) was added to a final concentration of 2 mg/ml into the MRS broth containing KCTC3179 cells. After shaking at 25° C. for 30 min, *Lactobacillus* were washed three times with fresh MRS broth and resuspended in the fresh MRS broth. After serial dilution, the treated cells were spread on MRS agar plate and incubated at 37° C. under anaerobic conditions. After 48 h, the mutant colonies were transferred into a separate well of 384-well plate containing 50 µl of MRS broth. The inoculated colonies were cultured under anaerobic condition at 37° C. without shaking. After overnight incubation, plate was replicated using a 384-pin replicator into two new plates, one with fresh MRS broth and another with the same broth containing 0.1 nCi/ml of $^{14}$C-palmitic acid. Then, plates were wrapped with parafilm and incubated at 37° C. for 30 min with gentle shaking. After incubation, 2 µl of the $^{14}$C-labeled culture in each well was transferred with a 384-pin replicator onto nylon membrane. After drying the membrane with the semi-dry system, the free $^{14}$C-palmitic acid in the bacterial spots on the membrane was removed by washing with MRS broth for three times. The washed membrane was exposed to X-ray film at –80° C. for 3 days. After development, the X-ray film was scanned and the relative dot density was analyzed with Gel-Pro™ analyzer software. High dot density colonies were selected and the strain with the most fatty acid extracting/robbing capability was identified and named as fatty acid robbing microbe 1 (FARM1). After obtaining FARM1 from NTG mutagenesis, 4-nitroquinoline 1-oxide (4NQO) was treated to FARM1 for generation of 2nd-round mutant FARM2 and ethylmethane sulphonate (EMS) was treated to FARM2 to generate 3rd-round mutant FARM3, respectively.

Evaluation of In Vitro Fatty Acid Extraction Capability

To evaluate the in vitro fatty acid extraction capability of identified strain, the radioactivity of *Lactobacillus* was measured after in vitro incubation with $^{14}$C labeled palmitic acid. First, *L. acidophilus* or identified FARM strains were inoculated into 2 ml of MRS broth and incubated. At the end of the exponential growth phase, the cell density was estimated again by measuring the absorbance at 600 nm. The cells were harvested by centrifugation and resuspended into fresh MRS broth containing 1 nCi/ml of $^{14}$C-palmitic acid. After an additional incubation for 1 h at 37° C., the $^{14}$C-labeled cells were washed 3 times with MRS broth. After resuspension in 1 ml of fresh MRS broth, 200 µl of the cell suspension were carefully transferred into a 4 ml scintillation vial containing 2 ml of liquid scintillation cocktail. The mixture was vigorously vortexed for 1 min and then the $^{14}$C activity was determined by a liquid scintillation spectrophotometry.

Evaluation of Acid Production Ability

For testing acid production, the *L. acidophilus* was cultured at 37° C. in MRS broth until the end of the exponential growth phase. One ml of cell culture was inoculated into a bottle containing 100 ml of sterile reconstituted skim milk (10%) and glucose (2%). The pH changes of yogurt were determined after incubation for 24 h, 48 h and 72 h, respectively. For cell growth measurement, 5 ml of the resultant yogurt after 48 h culture was transferred to a 15 ml conical tube and vortexed vigorously. Then, 1 ml of the homogenized sample was serially diluted with sterile PBS and 50 µl from each dilution was plated on a MRS plate. The plates were cultured under anaerobic conditions for 48 h to count the visible colonies.

Animal Experiment

All procedures performed with animals were in accordance with established guidelines and were reviewed and approved by the Institutional Animal Care and Use Committee. Male SD rats with body weight ranged at 200-220 g were housed two in each cage and provided normal rat food and water ad libitum during the first week. All animals were kept under 12-h light and dark cycle until the end of the experiment. The temperature was kept constant at 22±1° C. and the humidity was 40-50%. After 1 wk of familiarization in this environment, the rats were randomly divided into control or experimental groups (n=14 per group): control group (high fat diet only), 3179 group (high fat diet with yogurt fermented by *L. acidophilus* KCTC3179 strain), FARM group (high fat diet with yogurt fermented by FARM mutant, respectively). The high fat diet used in this study was made with standard rat food (complex-carbohydrate 60%, protein 22%, fat 3.5%, fiber 5%, crude ash 8%, calcium 0.6%, and phosphorus 1.2%) plus 20% pig lard. The composition of the high fat diet is as follows; complex-carbohydrate 48%, protein 17.6%, fat 22.8%, fiber 4%, crude ash 6.4%, calcium 0.48%, and phosphorus 0.96%. The yogurt for feeding was fermented with 10% non-fat milk, 2% sugar, and 1% of *L. acidophilus* culture at a concentration of $\geq 10^9$/ml. Through experiment periods, rats had free access to each diet while 3 ml of fermented yogurt was administered orally for the purpose of each experiment. Body weight was measured every week between 9 and 10 A.M after 12 h fasting.

1. Gastrointestinal Tract Colonization Ability

After 8 weeks of *L. acidophilus* feeding for colonization, four rats of each control or experimental group were randomly selected and killed under anesthesia with ether. The gastrointestinal organs including stomach and small intestine from rats were collected immediately and weighted. Samples were transferred into 50 ml conical tubes and diluted with sterile saline to give a 10-fold dilution (wt/vol). Then, samples in saline were homogenized with a homogenizer to release the content of gastrointestinal organs. After serial dilution, the homogenates were plated on a lactobacillus selective agar plates and incubated anaerobically for 48 h. The numbers of viable lactobacilli were assessed by counting the colonies formed in the selected plates and expressed as $\log_{10}$ CFU per gram (wet weight) of various regions of the gastrointestinal organs.

2. In Vivo Effect of Farms on the Induction of the Diet-Induced Obesity

The long-chain triglyceride, triolein, was used as the substrate in this experiment. [$^{14}$C] labeled triolein in benzene solution was kept at –70° C. until the day before use. About 1 µCi of [$^{14}$C] labeled triolein was added per ml of unlabeled triolein and the solvent was evaporated at RT under nitrogen for overnight. The triolein mixture was administered in an amount of 0.5 mmol/100 g of body weight to the animals after feeding *Lactobacillus* for 22 weeks. After oral administration, blood samples were collected by cardiac puncture at 120 min, 240 min, 360 min, 480 min and 600 min, respectively. 0.1 ml of each serum sample was mixed immediately with 1.8 ml of LSC and the $^{14}C$ activity was determined by a liquid scintillation spectrophotometry. In vivo effect of FARMs on the induction of the diet-induced obesity was investigated by measuring in vivo fatty acid absorption abilities of FARMs after feeding yogurt fermented with *Lactobacillus*.

3. MRI Analysis of the Visceral Fat Content

Magnetic resonance imaging (MRI) analysis was performed to measure the abdominal subcutaneous and visceral fat with a Bruker Biospec™ 47/40 4.7-Tesla instrument. Rats were anesthetized with a combination of Zoletil™ (25 mg/kg) and Rompun™ (10 mg/kg). To obtain images, the rats were placed prone position in the magnet. MRIs were recorded using the body coil as the transmitter and receiver. A series of T1-weighted transaxial scans for the measurement of intra-abdominal and subcutaneous fat were acquired from a region extending from 8 cm above to 8 cm below the 4th and 5th lumbar interspace. Intra-abdominal and subcutaneous fat areas were measured using an Image J program.

4. Serum Biochemical Analysis

Blood samples of experiment rats were collected at the beginning and at 22-wks to determine the serum biochemical values. All animals were fasted overnight prior to blood collection. The whole blood samples of the rats were collected by cardiac puncture under anesthesia with aether. After centrifugation at 2,000×g for 10 min at 4° C., serum samples were aliquoted and stored at −70° C. until analysis. Serum was analyzed for biochemical characteristics with available kits, such as insulin (Rat/Mouse ELISA kit), leptin (Leptin ELISA kit) and serum glucose levels (blood glucose meter). Serum total cholesterol, HDL-cholesterol, LDL-cholesterol, and triglyceride concentration was detected with ELISA kits.

5. Effect of FARM3 on Diet-Induced Obesity

The 3 month old male SD rats were given high-fat feed (described above) for 8 weeks to develop diet-induced obesity with average body weight of 425 g. The rats were randomly divided into groups (n=14 per group) and received fermented yogurt or drug under continued high-fat diet conditions: 3179 group (high fat diet with yogurt fermented by *L. acidophilus* KCTC 3179 strain), FARM3 group (high fat diet with yogurt fermented by FARM3 mutant), Orlistat™ (high fat diet with Xenical™ in an amount of 200 mg/kg diet).

6. Statistical Analysis

All data were expressed as mean±standard deviation. Statistical comparisons were performed by analysis of variance (ANOVA) test. A value of P<0.05 was considered statistically significant.

Results

Figure 1:
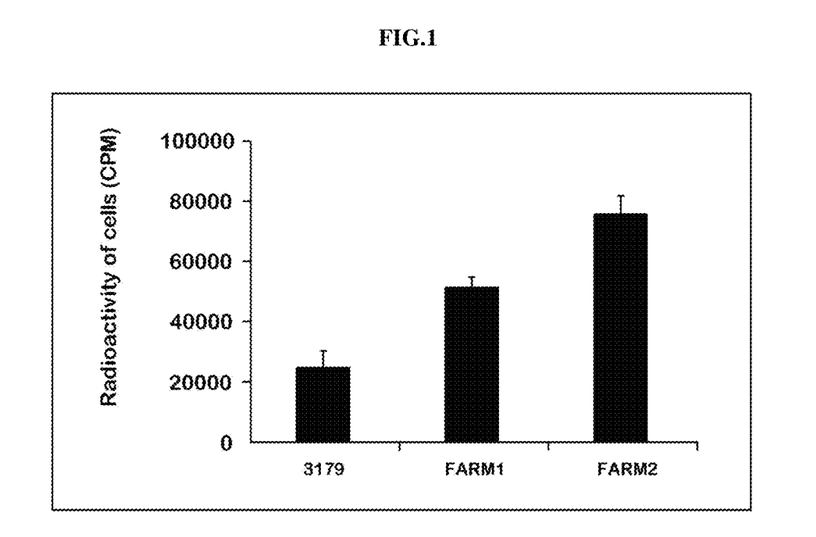
FIG. 1. is a graph illustrating Fatty acid extraction capability of FARM *Lactobacillus* in accordance with an exemplary aspect of the present invention.

1. Different Fatty Acid Extraction Capabilities of Farms and Reduction of Caloric Intake FIG. 1 shows the different fatty acid extraction capabilities of FARMs from their surrounding environment.

Fatty acid extraction capability of FARMs was inversely related to caloric intake by host in which its GI tract was colonized with FARMs. *Lactobacillus acidophilus* KCTC 3179 (labeled as "3179") were mutagenized with N-methyl-N-nitro-N-nitrosoguanidine (NTG) to generate FARM1 having increased fatty acid extraction capability. FARM1 was again mutagenized with 4-nitroquinoline 1-oxide (4NQO) to generate FARM2 having better FA extraction capability. FA extraction capabilities of FARMs were determined by measuring the radioactivity in Lactobacilli using liquid scintillation spectroscopy after incubation of Lactobacilli with 1 nCi/ml of $^{14}C$ labeled palmitic acid for 1 hour. Values are mean CPM±standard deviation (n=4).

Figure 2:
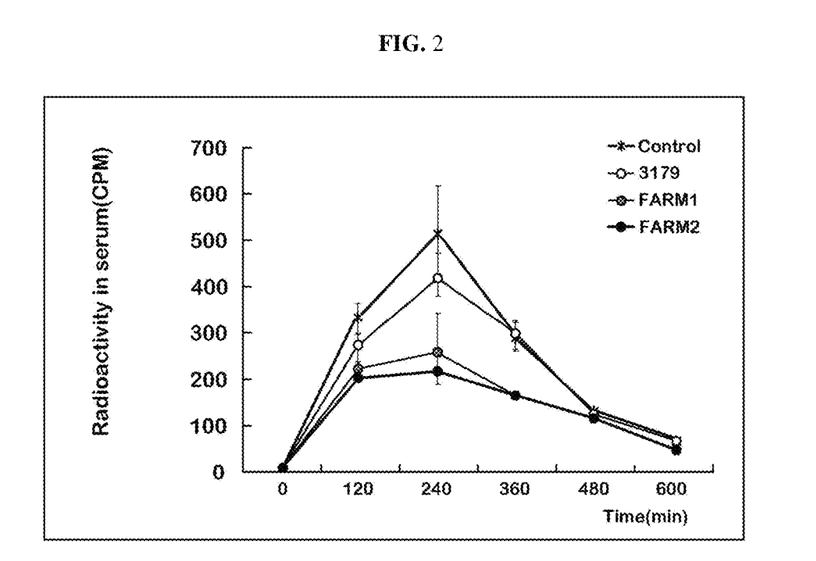
FIG. 2. is a graph illustrating the change of the caloric intake by host colonized with FARM *Lactobacillus* in accordance with an exemplary aspect of the present invention.

FIG. 2 shows the reduction of caloric intake in host that was colonized with FARMs. The GI tracts of the SD rats were colonized for 8 weeks with either FARMs or *L. acidophilus* KCTC 3179. After administration of $^{14}C$-labeled triolein into the rats colonized with different Lactobacilli (FARM1, FARM2, KCTC 3179) and rats without feeding of *Lactobacillus* (control), blood samples were collected for the analysis of radioactivity to determine the relative caloric intake by host.

The FA extraction capability of FARM is inversely correlated to the absorption of FA by host.

2. Acid Production Ability

Each of *Lactobacillus* cells was inoculated into the sterile reconstituted skim milk supplemented with 2% glucose to make yogurt. The pH values of the each yogurt were determined at the indicated time points (24 h, 48 h and 72 h) to measure their acidification activities. Values are means±SEM of 10 samples each.

Table 1 displays the acidification characteristics of milk by *Lactobacillus acidophilus* KCTC 3179, FARM1 and FARM2.

TABLE 1

Values are means + SEM of 10 samples each.

| | pH Values Of Yogurt | | |
|---|---|---|---|
| Time | 3179 | FARM1 | FARM2 |
| 24 | 6.78 ± 0.16 | 7.12 ± 0.16 | 6.59 ± 0.24 |
| 48 | 3.82 ± 0.24 | 4.42 ± 0.05 | 3.77 ± 0.14 |
| 72 | 3.66 ± 0.13 | 3.97 ± 0.12 | 3.69 ± 0.12 |

3. Colonization Ability in the GI Tract

After feeding rats yogurt fermented with *Lactobacillus acidophilus* KCTC 3179, FARM1 and FARM2 for 8 weeks each, the samples of stomach and small intestine from each group were taken to count the colonies forming unit (CFU). Control means rats without feeding any yogurt. Values are means±SEM of 5 samples each.

Table 2 displays the colonization of *Lactobacillus* KCTC 3179, FARM1 and FARM2 in the GI tract of rats.

TABLE 2

Values are means + SEMof5sampleseach.

| | $Log_{10}$[CFU of lactobacilli/g(wet weight) of organ] | |
|---|---|---|
| Strain | Stomach | Small Intestine |
| control | Non-detectable | 6.64 ± 0.22 |
| 3179 | 8.54 ± 0.20 | 8.64 ± 0.14 |
| FARM1 | 8.61 ± 0.19 | 8.50 ± 0.19 |
| FARM2 | 8.50 ± 0.22 | 8.63 ± 0.23 |

4. Colonization Ability Under Diet-Induced Obesity

After feeding rats high fat diet with yogurt fermented with *Lactobacillus acidophilus* KCTC 3179, FARM1 and FARM2 for 4 weeks each, the samples of stomach and small intestine from each sample were taken to count the colonies forming unit (CFU). Control means rats without feeding any yogurt. Values are means±SEM of 5 samples each.

Table 3 displays the colonization of *Lactobacillus* KCTC 3179, FARM1 and FARM2 in the GI tract of rats while inducing obesity by diet.

TABLE 3

Values are means + SEM of 5 samples each.

Log$_{10}$[CFU of lactobacilli/g (wet weight) of organ]

| Strain | Stomach | Small Intestine |
|---|---|---|
| control | Non-detectable | 5.98 ± 0.21 |
| 3179 | 8.15 ± 0.29 | 9.14 ± 0.24 |
| FARM1 | 8.32 ± 0.23 | 8.89 ± 0.22 |
| FARM2 | 8.19 ± 0.17 | 9.05 ± 0.19 |

5. The Effect of Caloric Extraction by FARMs in the GI Tract on the Induction of the Diet-Induced Obesity.

Figure 3:
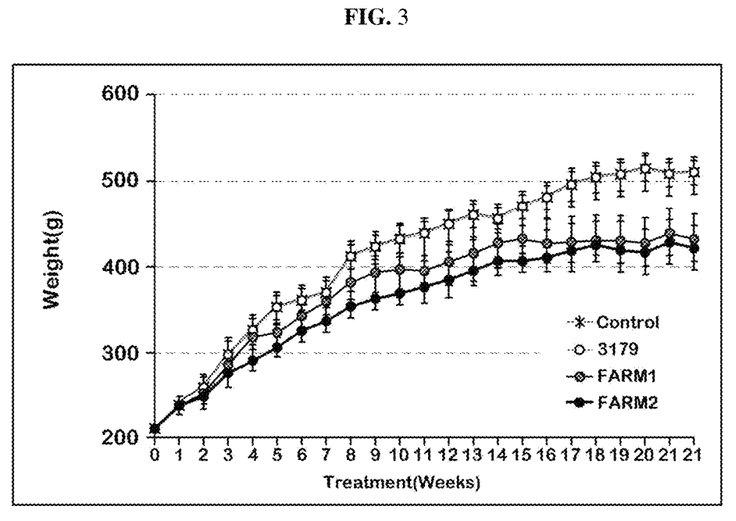
FIG. 3. is a graph illustrating the change in body weight of host colonized with FARM *Lactobacillus* in accordance with an exemplary aspect of the present invention.

FIG. 3 shows the changes in body weight of host that was colonized with *Lactobacillus*.

Three months old Male SD rats (200-220 g) were randomly divided into four groups (n=14 per group); rats fed high fat diet only (control) and rats fed with Lactobacilli (KCTC 3179, FARM1, or FARM2) daily for 22 weeks. Change in body weight is displayed as mean±SEM.

Figure 4:
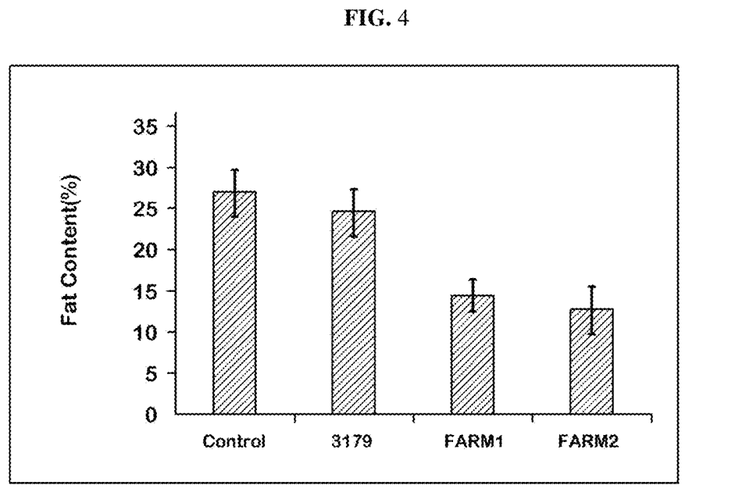
FIG. 4. shows visceral fat analysis of the host colonized with FARM *Lactobacillus* measured using MRI and analyzed with an image analysis program (Image J, USA) in accordance with an exemplary aspect of the present invention.

FIG. 4 shows the visceral fat analysis of host that was colonized with *Lactobacillus*. The visceral fat areas of the experiment groups of the rats were measured using Magnetic resonance imaging (MRI) after finishing the feeding experiment and analyzed with an image analysis program (Image J, USA). Differences in visceral fat accumulation among the experiment groups of the rats are displayed as mean±SEM.

Figure 5:
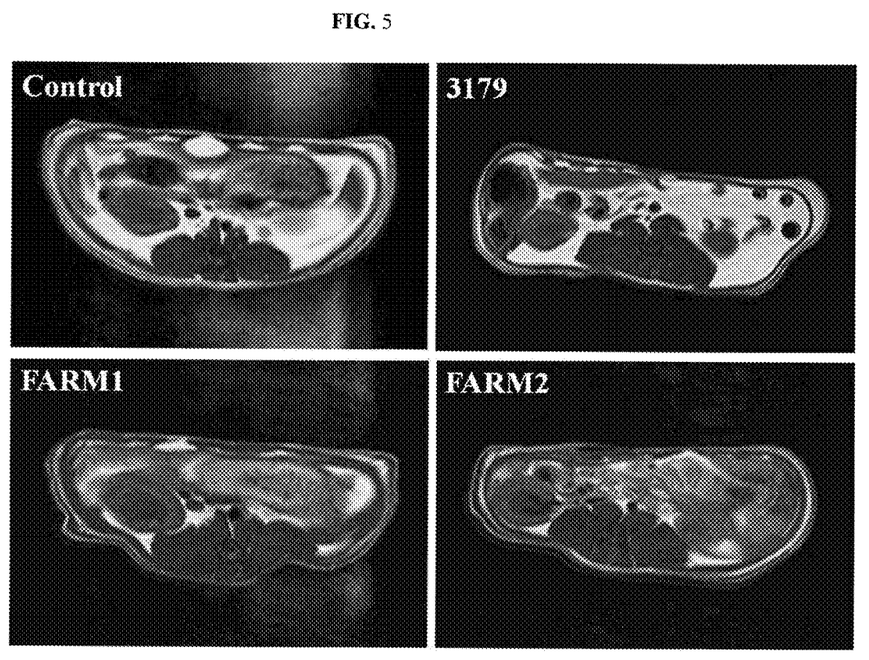
FIG. 5. shows MRI images of the visceral fat accumulation of the rats fed high fat diet only and with FARM daily after 22 weeks in accordance with an exemplary aspect of the present invention.

FIG. 5 shows the visceral fat images of MRI in host that were colonized with *Lactobacillus*.

Representative images of the visceral fat accumulation of the rats fed high fat diet only (control) and with Lactobacilli (KCTC 3179, FARM1, or FARM2) daily after 22 weeks.

6. The Comparison of the Blood Serum Parameters after Feeding *Lactobacillus* 3179 or FARM Strains Three months old Male SD rats (200-220 g) were randomly divided into four groups (n=14 per group), and fed high fat diet only or with Lactobacilli for 22 weeks; control group (high fat diet only), 3179 group (high fat diet with yogurt fermented by *L. acidophilus* KCTC 3179 strain), FARM group (high fat diet with yogurt fermented by FARM mutant, respectively). The blood samples of experimental rats were collected at the beginning and at the end of the experimental period, and analyzed for the change of the blood serum parameters. All data were expressed as mean±SEM. Statistical comparisons were performed by analysis of variance (ANOVA) test. A value of p<0.05 was considered statistically significant.

Figure 6:
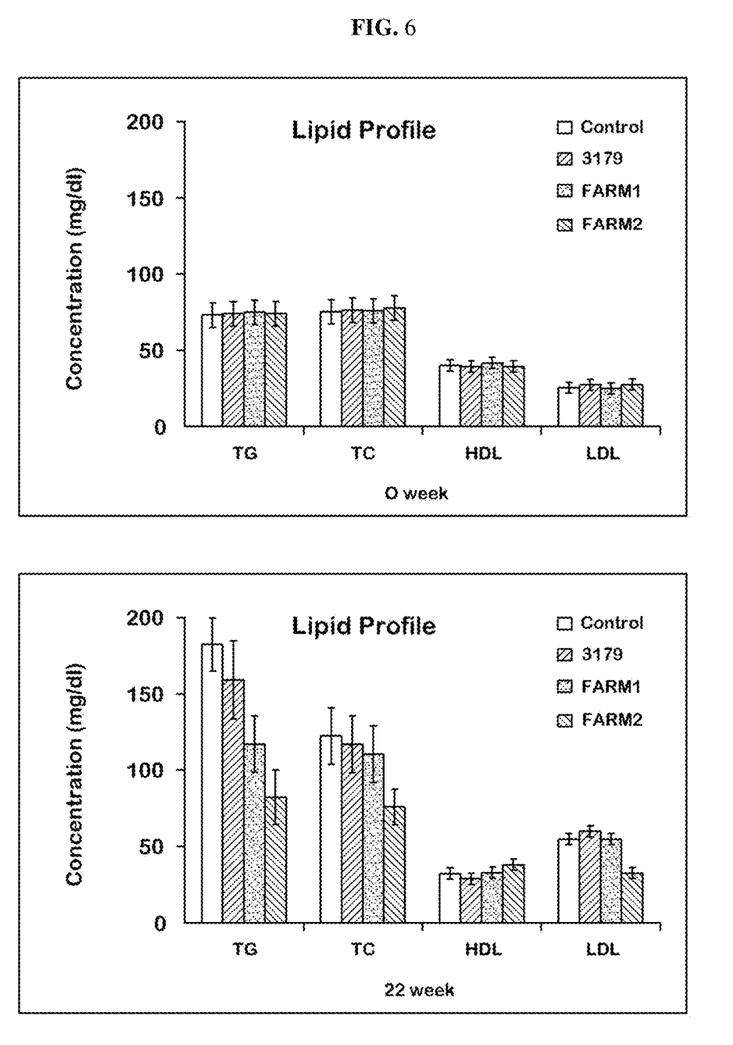
FIG. 6. shows a change of plasma lipid profiles in rats in accordance with an exemplary aspect of the present invention. (TG, as in triglycerides; TC, as in total cholesterol; HDL, as in high-density lipoprotein cholesterol; LDL, as in low-density lipoprotein cholesterol)

FIG. 6 shows the change of plasma lipid profiles in rats. TG, triglycerides; TC, total cholesterol; HDL, high-density lipoprotein cholesterol; LDL, low-density lipoprotein cholesterol.

Figure 7:
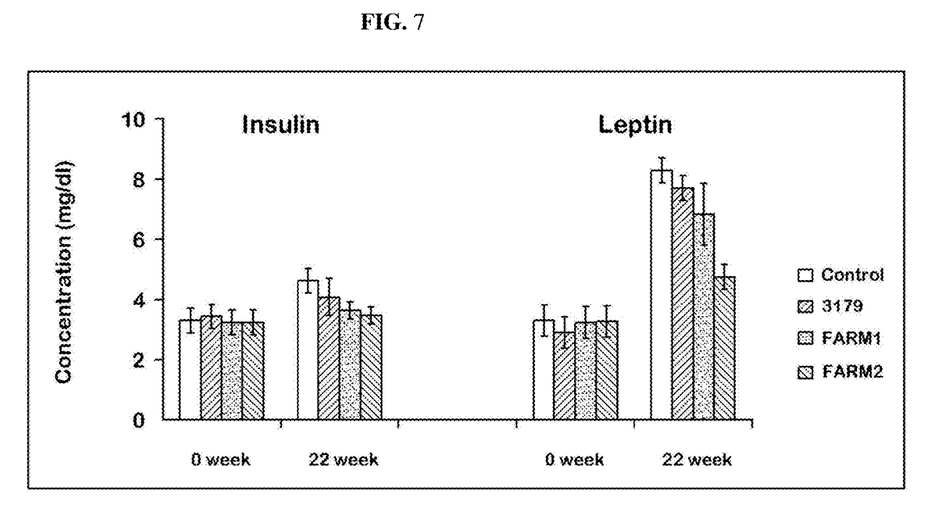
FIG. 7. shows a change of plasma insulin and leptin concentrations in rats in accordance with an exemplary aspect of the present invention.

FIG. 7 shows the change of plasma insulin and leptin concentrations in rats.

Figure 8:
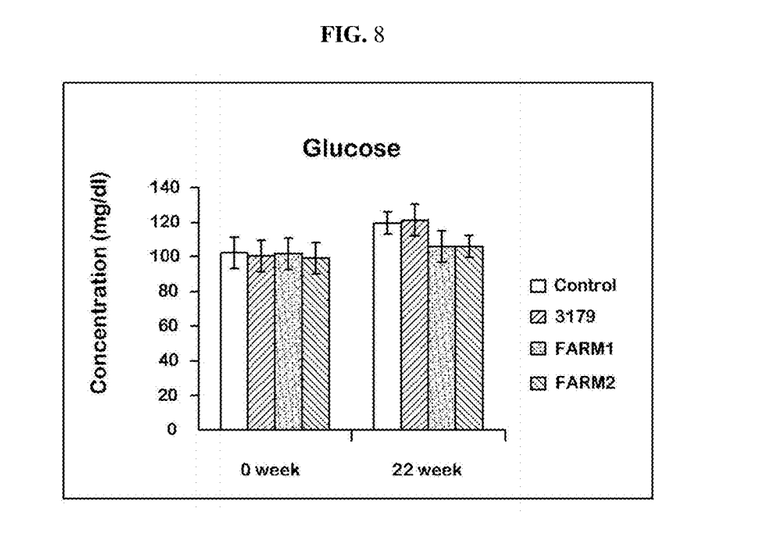
FIG. 8. shows a change of blood glucose concentrations in rats in accordance with an exemplary aspect of the present invention.

FIG. 8 shows the change of blood glucose concentrations in rats.

7. Effect of FARM3 on Diet-Induced Obesity

Figure 9:
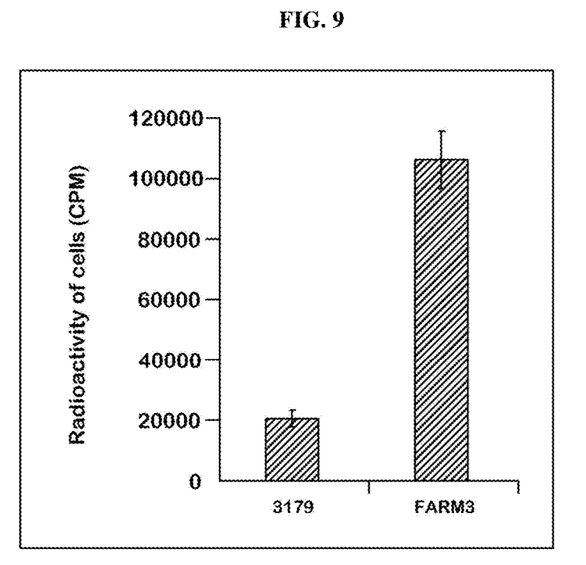
FIG. 9. illustrates the comparison of in vitro FA absorption capacity of FARM *Lactobacillus* in accordance with an exemplary aspect of the present invention.

FIG. 9 shows in vitro fatty acid extraction capability of FARM3 from their surrounding environment. FARM2 was mutagenized with ethylmethane sulphonate (EMS) to generate FARM3 with better fatty acid extraction capability. Fatty acid extraction capability of FARM3 was determined by measuring the radioactivity in Lactobacilli using liquid scintillation spectroscopy after incubation of Lactobacilli with 1 nCi/ml of 14C labeled palmitic acid for 1 hour. Values are mean±standard deviation (n=4).

Figure 10:
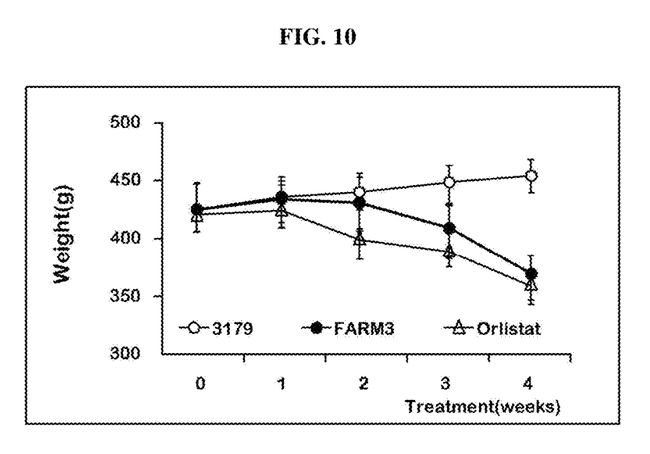
FIG. 10. illustrates the reduction of caloric intake by FARM *Lactobacillus* or Orlistat in accordance with an exemplary aspect of the present invention.

FIG. 10 shows the reduction of caloric intake by *Lactobacillus* or Orlistat™

The 3 month old male SD rats were given high-fat feed for 8 weeks to develop diet-induced obesity with average body weight of 425 g. The diet-induced obese rats were administered daily yogurt fermented with wild-type *Lactobacillus* 3179 (○, high fat diet with yogurt fermented by *L. acidophilus* KCTC3179 strain), yogurt fermented with FARM3 (●, high fat diet with yogurt fermented by FARM3) or Orlistat™ (Δ, high fat diet with Xenical™ 200 mg/kg diet) under continued high-fat diet condition for 4 weeks. Change in body weight (n=14) is displayed as mean±SEM.

The invention claimed is:

1. A pharmaceutical composition for treatment of obesity and obesity related metabolic syndrome, comprising treated microorganisms which can colonize the gastrointestinal tract of mammals and reduce free fatty acids absorbed into the body of a host by absorbing the free fatty acids in the gastrointestinal tract of mammals, wherein the treated microorganisms comprise mutant microorganisms mutagenized from gut microbiota, wherein the mutant microorganisms comprise probiotic strains subjected to chemical mutagenesis, and wherein the mutant microorganism is selected from the group consisting of *Lactobacillus acidophilus* FARM1 KCTC 11513BP; *Lactobacillus acidophilus* FARM2 KCTC 11514BP; and *Lactobacillus acidophilus* FARM3 KCTC 11515BP.

2. A pharmaceutical composition for treatment of obesity and obesity related metabolic syndrome, comprising treated microorganisms which can colonize the gastrointestinal tract of mammals and reduce free fatty acids absorbed into the body of a host by absorbing the free fatty acids in the gastrointestinal tract of mammals, wherein the treated microorganisms comprise, mutant microorganisms mutagenized from gut microbiota and providing enhanced fatty acid absorption capability, wherein the mutant microorganisms are derived from probiotic strains subjected to chemical mutagenesis, and wherein the mutant microorganism is selected from the group consisting of *Lactobacillus acidophilus* FARM1 KCTC 11513BP; *Lactobacillus acidophilus* FARM2 KCTC 11514BP; and *Lactobacillus acidophilus* FARM3 KCTC 11515BP.

* * * * *